US010940326B2

(12) United States Patent
Fang et al.

(10) Patent No.: US 10,940,326 B2
(45) Date of Patent: Mar. 9, 2021

(54) DEVICE WITH HIGH ENERGY ROTATING MAGNET AND MASSAGE CHAIR STRUCTURE WITH ROTATING MAGNET

(71) Applicant: Zhejiang Heye Health Technology Co., Ltd., Huzhou (CN)

(72) Inventors: Zhicai Fang, Huzhou (CN); Lijiang Hu, Huzhou (CN); Jun Li, Huzhou (CN)

(73) Assignee: Heye Health Technology Co., Ltd., Huzhou (CN)

( * ) Notice: Subject to any disclaimer, the term of this patent is extended or adjusted under 35 U.S.C. 154(b) by 204 days.

(21) Appl. No.: 16/072,302

(22) PCT Filed: Jan. 25, 2017

(86) PCT No.: PCT/CN2017/072579
§ 371 (c)(1),
(2) Date: Jul. 24, 2018

(87) PCT Pub. No.: WO2017/133614
PCT Pub. Date: Aug. 10, 2017

(65) Prior Publication Data
US 2019/0022403 A1    Jan. 24, 2019

(30) Foreign Application Priority Data
Feb. 3, 2016  (CN) .......................... 201610075463.3

(51) Int. Cl.
*A61N 2/12*      (2006.01)
*A61H 23/02*     (2006.01)

(52) U.S. Cl.
CPC ........... *A61N 2/12* (2013.01); *A61H 23/0254* (2013.01); *A61H 2201/0149* (2013.01)

(58) Field of Classification Search
CPC ........ A61H 23/0254; A61H 2201/0149; A61N 2/12
(Continued)

(56) References Cited

U.S. PATENT DOCUMENTS 4,422,449 A * 12/1983 Hamabe ................... A61H 1/00
                                                    601/102
4,576,149 A *  3/1986 Otuka ...................... A61H 1/00
                                                    601/116
(Continued)

FOREIGN PATENT DOCUMENTS

CN         202161527      3/2002
CN           2614701      5/2004
(Continued)

OTHER PUBLICATIONS

English Translation of CN1788810, Tian Zhongshu CUI, Jun. 21, 2006 (see attached) (Year: 2006).*
(Continued)

*Primary Examiner* — Navin Natnithithadha
*Assistant Examiner* — Sunita Reddy
(74) *Attorney, Agent, or Firm* — Dragon Sun Law Firm, PC; Jinggao Li, Esq.

(57) ABSTRACT

The present disclosure relates to the technical field of equipment with a rotating magnetic field. Disclosed are a device with a high energy rotating magnet and a massage chair structure with a rotating magnet. The present disclosure includes a vertically driven revolving axle connected to a motor. A top end of the vertically driven revolving axle is connected to a gear set. The gear set meshes with a driving gear. A base revolving plate is fixed on an upper portion of the driving gear. A magnetic assembly is installed on the
(Continued)

base revolving plate. The present disclosure offers improved physical performance, low cost, and an enhanced effect of magnetic therapy.

12 Claims, 8 Drawing Sheets

(58) Field of Classification Search
USPC .................................................. 600/9–15
See application file for complete search history.

(56) References Cited

U.S. PATENT DOCUMENTS

| | | | | |
|---|---|---|---|---|
| 5,776,085 | A * | 7/1998 | Stone | A61H 37/00 600/594 |
| 5,817,000 | A * | 10/1998 | Souder | A61N 2/06 600/15 |
| 6,001,055 | A * | 12/1999 | Souder | A61N 2/008 600/9 |
| 6,030,033 | A * | 2/2000 | Schultz | A47C 1/035 297/340 |
| 6,224,563 | B1 * | 5/2001 | Nonoue | A61H 15/0078 601/99 |
| 6,832,991 | B1 * | 12/2004 | Inada | A61H 39/04 601/100 |
| 6,979,300 | B1 * | 12/2005 | Julian | A61H 7/00 601/15 |
| 2001/0011160 | A1 * | 8/2001 | Oguma | A61H 7/004 601/89 |
| 2004/0158176 | A1 * | 8/2004 | Park | A61H 39/04 601/18 |
| 2005/0115343 | A1 * | 6/2005 | Sakamaki | B60N 2/0232 74/89.23 |
| 2005/0221959 | A1 * | 10/2005 | Yeh | A61H 7/001 482/54 |
| 2006/0142676 | A1 * | 6/2006 | Fujii | A61H 15/0078 601/98 |
| 2006/0255630 | A1 * | 11/2006 | Tseng | A47C 1/0347 297/30 |
| 2008/0009777 | A1 * | 1/2008 | Chiu | A61H 15/00 601/99 |
| 2008/0097260 | A1 * | 4/2008 | Tsukada | A61H 15/0078 601/98 |
| 2009/0177128 | A1 * | 7/2009 | Fukuyama | A61H 15/0078 601/98 |
| 2010/0081858 | A1 * | 4/2010 | Sotiriou | A61N 2/12 600/13 |
| 2013/0088059 | A1 * | 4/2013 | Nagamitsu | A47C 3/02 297/260.2 |
| 2014/0217792 | A1 * | 8/2014 | Meyer | B60N 2/5685 297/284.8 |
| 2020/0046127 | A1 * | 2/2020 | Levin | A47C 1/0308 |

FOREIGN PATENT DOCUMENTS

| | | |
|---|---|---|
| CN | 2778259 | 5/2006 |
| CN | 1788810 | 6/2006 |
| CN | 2933383 | 8/2007 |
| CN | 201143340 | 11/2008 |
| CN | 201469909 | 5/2010 |
| CN | 102309819 | 1/2012 |
| CN | 202120702 | 1/2012 |
| CN | 203090265 | 7/2013 |
| CN | 103295728 | 9/2013 |
| CN | 103656860 | 3/2014 |
| CN | 103751913 | 4/2014 |
| CN | 103892986 | 7/2014 |
| CN | 203676557 | 7/2014 |
| CN | 2722396 | 8/2015 |
| CN | 104958837 | 10/2015 |
| CN | 205612878 | 10/2016 |
| JP | 2006110316 | 4/2006 |
| KR | 100982947 | 9/2010 |

OTHER PUBLICATIONS

International Search Report for corresponding PCT/CN2016/105142.
The First Office for the Chinese Patent Application 201610075463.3.
Search report for the Chinese Patent Application 201610075463.3.
Written Opinion and notifications for corresponding PCT/CN2016/105142.

* cited by examiner

US 10,940,326 B2

DEVICE WITH HIGH ENERGY ROTATING MAGNET AND MASSAGE CHAIR STRUCTURE WITH ROTATING MAGNET

CROSS-REFERENCE TO RELATED APPLICATIONS

This application claims priority from PCT Application No. PCT/CN2017/072579, filed Jan. 25, 2017 and CN Application No. 201610075463.3, filed Feb. 3, 2016, the contents of which are incorporated herein in the entirety by reference.

TECHNICAL FIELD

The present disclosure relates to the technical field of equipment with a rotating magnetic field, and in particular to a device with a high energy rotating magnet and a massage chair structure with a rotating magnet.

BACKGROUND

Lots of existing furniture, massage health-care equipment, medical equipment, etc. have begun to use rotating magnetic field related equipment, but the existing technology of the gyromagnetic equipment is not mature enough, and the gyromagnetic equipment used does not have a stable enough structure, has the problems of high motor power, high energy consumption, large occupied space, high vibrations, high noise, poor heat dissipation and the like, has the defects of poor physical properties, insufficient magnetic field distribution, low effective utilization, usually not conducive to the setting of strong magnetic fields, high production costs, magnetic health care. The effect is not good.

SUMMARY OF THE DISCLOSURE

One objective of the present disclosure is to provide a device with a high energy rotating magnet having the advantages of favorable physical properties, low cost and favorable magnetic therapy effect.

The above technical objective of the present disclosure is achieved by the following technical solution: a device with a high energy rotating magnet comprises a vertically driven revolving axle, the vertically driven revolving axle is connected to a motor, an upper end of the vertically driven revolving axle is connected to a gear set, the gear set meshes with a driving gear, a base revolving plate is fixed on an upper portion of the driving gear, and a magnetic assembly is installed on the base revolving plate.

In the above technical solution, the whole structure has better stability and more optimized stress distribution, can adopt a low-power motor to perform low-power operations, and has the beneficial effects of low energy consumption, small occupied space, low vibrations, low noise and better heat dissipation effect. Besides, the magnetic assembly in the structure can be a magnetic assembly with super magnetism, and thus, a space intense magnetic field with more optimized distribution is formed.

The magnetic field has higher availability, which is beneficial to the effect of the intense magnetic field, so the magnetic therapy effect is better. The gear set can be a single gear, a change gear combination or a gear case to further reduce the motor power, so that a low-power motor can meet the high load demand, and speed change can be implemented. The base revolving plate acts as a carrier for producing the rotating magnetic field, and the driving gear is driven by the motor to operate such that the base revolving plate can rotate.

As a preferred aspect of the present disclosure, an assembly carrier is arranged below the driving gear, so as to enhance the assemblability and operation fluency and reduce the failure rate, thereby further optimizing the structure and stress distribution, enhancing various physical properties and having a better magnetic therapy effect.

As a preferred aspect of the present disclosure, the assembly carrier comprises a carrier bearing, so as to enhance the assemblability and operation fluency and reduce the failure rate, thereby further optimizing the structure and stress distribution, enhancing various physical properties and having a better magnetic therapy effect.

As a preferred aspect of the present disclosure, a bearing outer ring of the carrier bearing is installed on a supporting frame, the driving gear is arranged above a bearing inner ring of the carrier bearing, a rotary auxiliary bearing is arranged in a central region of the driving gear, and the supporting frame is provided with a center post over which an inner ring of the rotary auxiliary bearing is sleeved, so as to enhance the assemblability and operation fluency and reduce the failure rate, thereby further optimizing the structure and stress distribution, enhancing various physical properties and having a better magnetic therapy effect.

As a preferred aspect of the present disclosure, a motor outer protective cover is arranged on the outer side of the motor, thereby performing a favorable protective function, reducing the magnetic field of the external magnetic assembly, dust and other interference, and ensuring the effectiveness and service life of the motor.

As a preferred aspect of the present disclosure, the magnetic assembly comprises a base main pole block installed on the base revolving plate, thereby further optimizing the structure and stress distribution, enhancing various physical properties and having a better magnetic therapy effect.

As a preferred aspect of the present disclosure, the magnetic assembly further comprises an upper main pole block, and the upper main pole block is arranged on an upper portion of the base main pole block, thereby further optimizing the structure and stress distribution, enhancing various physical properties and having a better magnetic therapy effect.

As a preferred aspect of the present disclosure, the magnetic assembly further comprises an auxiliary pole block, and the auxiliary pole block is arranged on a lateral side of the upper main pole block, thereby further optimizing the structure and stress distribution, enhancing various physical properties and having a better magnetic therapy effect. By using the combined structure, the magnetic assembly can achieve a very strong superficial magnetic field, and the processing cost of a single strong magnetic block can be lowered, thereby being beneficial to optimization of the structure and enhancement of various properties.

As a preferred aspect of the present disclosure, a protective cover is sleeved over the outer side of the magnetic assembly, so as to provide a beautiful appearance, prevent the pole block from being oxidized, prevent the ferromagnetic object from direct collision and contact with the pole block, and also prevent the magnetic assembly from falling off in the high-speed operation process, thereby further optimizing the structure and stress distribution, enhancing various physical properties and having a better magnetic therapy effect.

As a preferred aspect of the present disclosure, a lower portion of the protective cover extends to form a cover installation piece for fixed connection with the base revolving plate, so as to ensure the installation stability of the protective cover, thereby further optimizing the structure and stress distribution, enhancing various physical properties and having a better magnetic therapy effect.

As a preferred aspect of the present disclosure, the protective cover is a non-magnetic isolation stainless steel cover, thereby further optimizing the structure and stress distribution, enhancing various physical properties and having a better magnetic therapy effect.

As a preferred aspect of the present disclosure, the base revolving plate is a magnetoconductive plate, thereby further optimizing the structure and stress distribution, enhancing various physical properties and having a better magnetic therapy effect. The magnetoconductive plate can be an iron plate, a steel plate or a plate of another magnetoconductive material.

The present disclosure has the following beneficial effects: the whole structure has better stability and more optimized stress distribution, can adopt a low-power motor to perform low-power operations, and has the advantages of low energy consumption, small occupied space, low vibrations, low noise and better heat dissipation effect. Besides, the magnetic assembly in the structure can be a magnetic assembly with super magnetism, and thus, a space intense magnetic field with more optimized distribution is formed. The magnetic field has higher availability, and is beneficial to the effect of the intense magnetic field, so the magnetic therapy effect is better. The gear set can be a single gear, a change gear combination or a gear case to further reduce the motor power, so that a low-power motor can meet the high load demand, and speed change can be implemented.

Another objective of the present disclosure is to provide a massage chair structure with a rotating magnet having the advantages of safe and reliable structure, high maneuverability, low cost and favorable magnetic therapy effect. Any one of the above devices with a high energy rotating magnet is arranged below a seat of the massage chair structure with a rotating magnet, a liftable telescopic footrest mechanism for foot resting is arranged between the seat and a chair bottom of the massage chair structure with a rotating magnet, the telescopic footrest mechanism comprises a reclining rod hinged to the seat and adjacent to the front side of the device with a high energy rotating magnet, a curved rod hinged to the other end of the reclining rod and located below the front portion of the device with a high energy rotating magnet and a retractable cylinder hinged to the other end of the curved rod and located below the device with a high energy rotating magnet, a piston rod of the retractable cylinder is hinged to a lower support rod, the other end of the lower support rod is hinged to a position of the chair bottom adjacent to the front end, and a rear end of the retractable cylinder is hinged to a position of the chair bottom adjacent to the rear end.

Figure 1:
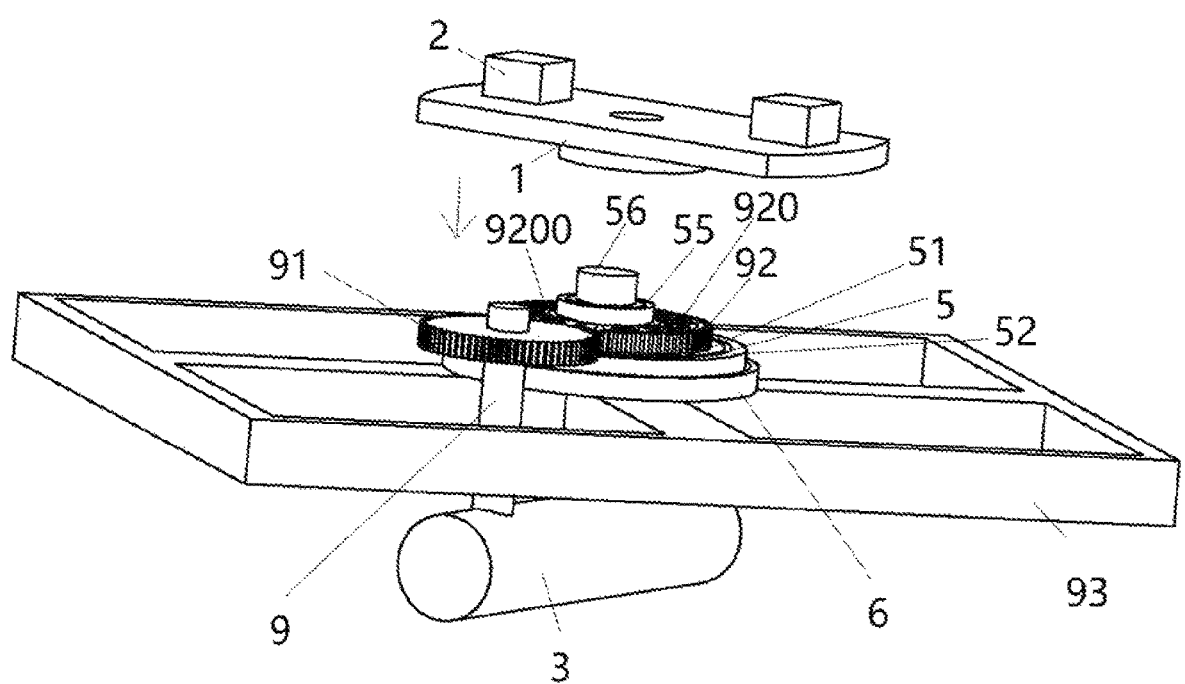
FIG. 1 is a disassembly-assembly schematic perspective view when a base revolving plate and a driving gear have not been assembled according to embodiment 1 of the present disclosure.

In the drawings: 9. vertically driven revolving axle, 3. motor, 91. gear set, 92. driving gear, 93. supporting frame, 1. base revolving plate, 2. magnetic assembly, 5. carrier bearing, 51. bearing inner ring, 52. bearing outer ring, 55. rotary auxiliary bearing, 56. center post, 71. base main pole block, 72. upper main pole block, 73. auxiliary pole block, 8. protective cover, 80. cover installation piece, 777. vertical screw hole, 778. vertical bolt, 779. nut, 7799. nut placement slot, 888. transverse screw hole, 889. transverse bolt, 6. bearing seat, 920. fixed installation hole, 990. seat, 991. chair bottom, 992. retractable footrest mechanism, 993. reclining rod, 994. curved rod, 995. retractable cylinder, 996. piston rod, 997. lower support rod, 9200. gear stiffener.

DETAILED DESCRIPTION OF THE DISCLOSURE

The present disclosure will be further described in detail below with reference to the accompanying drawings.

Figure 2:
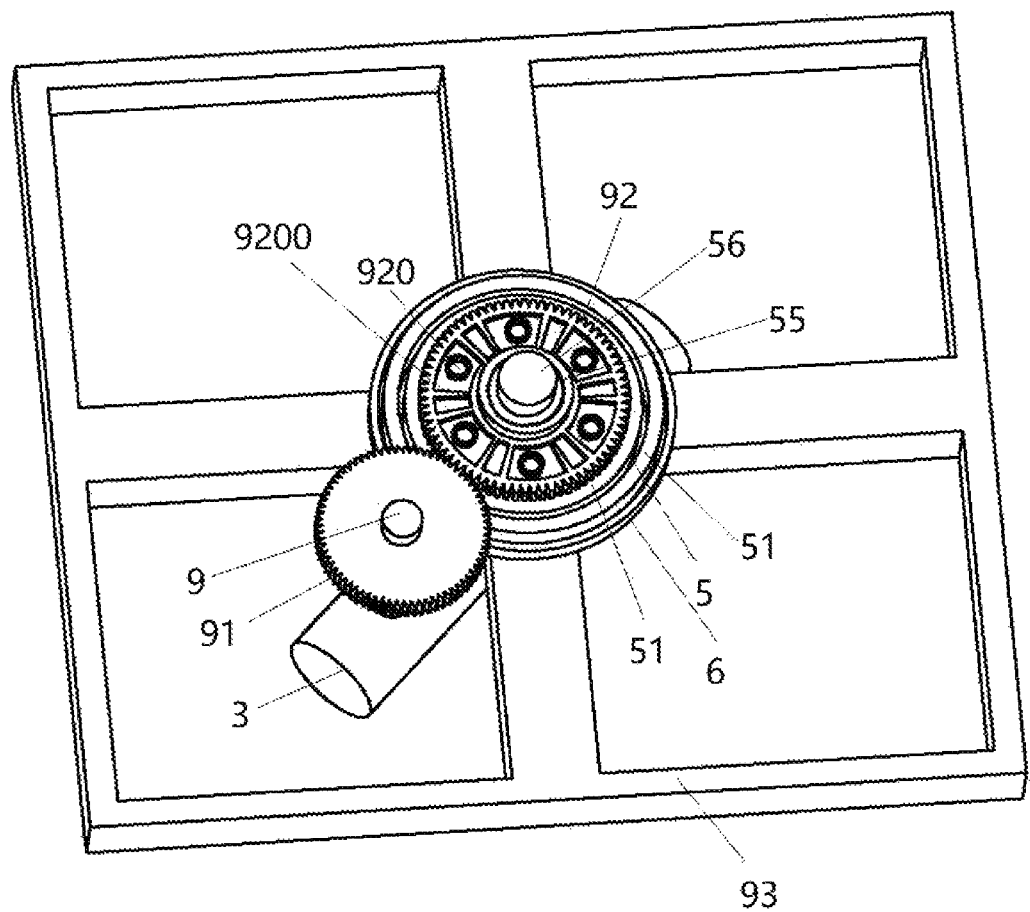
FIG. 2 is a schematic perspective view of various components connected to a supporting frame when the base revolving plate and the driving gear have not been assembled according to embodiment 1 of the present disclosure.

Embodiment 1. As shown in FIG. 1 and FIG. 2, a device with a high energy rotating magnet comprises a vertically driven revolving axle 9, the vertically driven revolving axle 9 is connected to a motor 3, an upper end of the vertically driven revolving axle 9 is connected to a gear set 91, the gear set 91 meshes with a driving gear 92, a base revolving plate 1 is fixed on an upper portion of the driving gear 92, and a magnetic assembly 2 is installed on the base revolving plate 1. The gear set 91 can be a single gear, a change gear combination or a gear case to further reduce the motor power, so that a low-power motor can meet the high load demand, and speed change can also be implemented. The base revolving plate 1 is placed as flat as possible and is preferably arranged such that the outer shape is axisymmetric or centrally symmetric. The number of the magnetic assemblies 2 is preferably an even number, and the magnetic assemblies are arranged around the central region; the magnetic assembly 2 in the present disclosure may adopt a structure of a single high-magnetism pole block with a strong magnetic field or a simple superposition of several existing pole blocks; and in embodiment 2, there is also a new composite structure of multiple pole blocks, so that the structure is optimized, and the magnetic field intensity on the surface of the pole block can be enhanced to an ultra-strong magnetic field that is difficult to achieve by a single pole block. An assembly carrier is arranged below the driving gear 92; the assembly carrier not only can implement effective cooperation with the driving gear 92, but also can carry the heavy weight of the upper portion and reduce the motor load, so that the abrasion of the motor bearing is reduced, and the required power is lowered, thereby prolonging the service life of the motor, lowering the temperature rise of the motor, and ensuring the stability of the whole structure in the operation process; and furthermore, the arrangement of the assembly carrier should not influence the normal rotation of the base revolving plate 1, and should ensure the effective and smooth rotation of the base revolving plate 1.

The assembly carrier comprises a carrier bearing 5, the carrier bearing 5 is also placed as flat as possible, and the carrier bearing 5 may preferably be a radial bearing, and further, may be a radial sealed bearing. According to the device of the present application, the rotation speed of the motor 3 can be adjusted according to the magnetic field required by the human body, and an alternating dynamic magnetic field is generated in the rotation process, so that the human body is in an alternating dynamic magnetic field, and the biological magnetic field of the human body is adjusted and changed, thereby regulating the microcirculation of the human body and treating corresponding diseases of the human body. In addition, the base revolving plate 1 is preferably a magnetoconductive plate, for example, may be an iron plate, a steel plate or a plate of another magnetoconductive material.

A bearing outer ring 52 of the carrier bearing 5 is installed on a supporting frame 93, the driving gear 92 is arranged above a bearing inner ring 51 of the carrier bearing 5, a rotary auxiliary bearing 55 is arranged in a central region of the driving gear 92, and the supporting frame 93 is provided with a center post 56 over which an inner ring of the rotary auxiliary bearing 55 is sleeved. The supporting frame 93 may be of a frame structure shaped like a Chinses character 'tian', that is, the outer side is a rectangular frame and two reinforcing ribs are cross-connected to form a cross shape in the frame; the center post 56 may be arranged in the crossed position of the two reinforcing ribs along the vertical direction; meanwhile, the supporting frame 93 may also be provided with a bearing seat 6 in the region adjacent to the crossed position of the two reinforcing ribs; and the bearing seat 6 is provided with an annular stepped slot portion for the carrier bearing 5 to be placed and the bearing outer ring 52 to be erected and assembled. The structure greatly increases the assemblability, enhances the assembly effect, and can reduce the failure rate. After the connection is implemented by this structure, the load carried by a motor rotor is greatly lowered, thereby reducing the abrasion of the motor bearing, lowering the required power, prolonging the service life of the motor and lowering the temperature rise of the motor. The driving gear 92 is provided with a plurality of fixed installation holes 920 in a circumferential array along the gear surface, and is fixedly connected with the base revolving plate 1 through retaining members such as bolts; the base revolving plate 1 may be provided with corresponding installation holes; and meanwhile, the driving gear 92 may be integrally formed with gear stiffeners 9200 in a circumferential array and arranged between adjacent fixed installation holes 920. The motor 3 may be arranged on the supporting frame 93, and the motor 3 and the base revolving plate 1 are arranged on two sides of the supporting frame 93 respectively; the motor 3 may be arranged upright; a motor shaft of the motor 3 may be directly used as a vertically driven revolving axle 9, or the motor 3 may be horizontally arranged while the motor shaft thereof is used as a drive shaft and connected to another revolving axle through the existing variable-direction transmission connection structure such as a bevel gear, and then the revolving axle may be used as the vertically driven revolving axle 9; and at this time, the vertically driven revolving axle 9 may be perpendicular to the motor shaft of the motor 3.

A motor outer protective cover is arranged on the outer side of the motor 3, and the motor outer protective cover may be a magnetoconductive material cover, so that the external magnetic lines of force can be diverted without affecting the motor.

Figure 3:
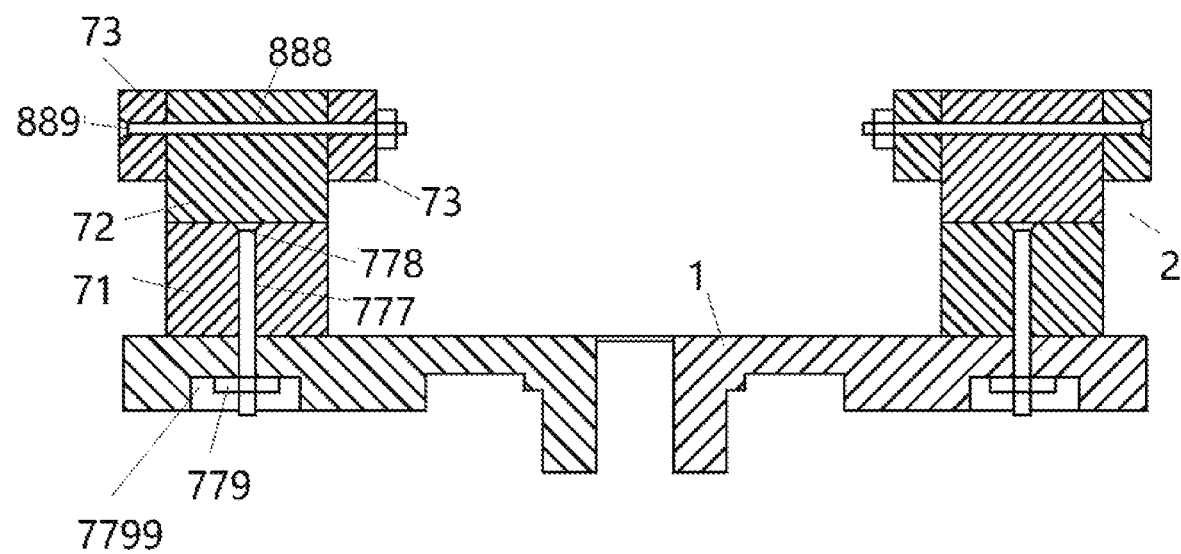
FIG. 3 is a cross-sectional structural view after the base revolving plate is assembled with a magnetic assembly according to embodiment 2 of the present disclosure.
Figure 4:
FIG. 4 is a pole distribution diagram when two magnetic assemblies are arranged in embodiment 2 of the present disclosure.

Embodiment 2. As shown in FIG. 3 and FIG. 4, the difference from embodiment 1 lies in the design of the magnetic assembly 2. In the present embodiment, according to a first solution, the magnetic assembly 2 comprises a base main pole block 71 installed on the base revolving plate 1, and the base main pole block 71 may be independently used directly as a magnetic assembly 2, and may also be a rectangular parallelepiped or cubic pole block with high surface magnetic field intensity. According to a second solution, the magnetic assembly 2 not only comprises a base main pole block 71, but also comprises an upper main pole block 72, the upper main pole block 72 is arranged on the upper portion of the base main pole block 71, the upper main pole block 72 may also be a rectangular parallelepiped or cubic pole block with high surface magnetic field intensity, and the upper main pole block 72 and the base main pole block 71 may have identical or similar size and identical or similar surface magnetic field intensity; of course, a pole block similar to the upper main pole block 72 or the base main pole block 71 may also be arranged above the upper main pole block 72, the base main pole block 71 is connected with the base revolving plate 1, the base main pole block 71 is provided with a vertical screw hole 777 running through the top and bottom, the base revolving plate 1 is provided with a corresponding installation screw hole, and a vertical bolt 778 is arranged in the vertical screw hole 777 and the vertical bolt 778 passes through the installation screw hole in the base revolving plate 1 and is locked by a nut 779; further, the lower position of the base revolving plate 1 may be provided with a nut placement slot 7799 which correspondingly communicates with the installation screw hole and is for the nut 779 to be placed; in addition, the highest point of the vertical bolt 778 does not exceed the top surface of the base main pole block 71, the poles of the base main pole block 71 and the upper main pole block 72 are respectively arranged along the vertical direction with the adjacent sides having the same polarity; in this way, the base main pole block 71 and the upper main pole block 72 may be sucked up and down, and the top surface of the base main pole block 71 and the bottom surface of the upper main pole block 72 are in seamless connection and close contact; and in this structure, the magnetic assembly 2 is effectively fixed on the base revolving plate 1, thereby preventing the base main pole block 71 from generating top leakage magnetic flux due to the opening, and ensuring the reliability and safety of the mechanical connection between the magnetic assembly 2 and the base revolving plate 1. A third solution is implemented based on the second solution: the magnetic assembly 2 further comprises an auxiliary pole block 73, the auxiliary pole block 73 is arranged on the lateral side of the upper main pole block 72, the size and surface magnetic field intensity of the auxiliary pole block 73 may be less than those of the upper main pole block 72 or the base main pole block 71, and the auxiliary pole block 73 may be a rectangular parallelepiped or cubic pole block, is arranged at a position, adjacent to the top as far as possible, of the upper main pole block 72, and may contact the lateral side of the upper main pole block 72 and have a sufficient distance from the base revolving plate 1 without contact, thereby avoiding the magnetic short circuit and magnetism drop of the auxiliary pole block 73, and also saving the magnetic material. There may be multiple auxiliary pole blocks 73, for example, two auxiliary pole blocks 73 are arranged and located on two opposite sides of the upper main pole block 72 to form a T-shaped structure, or multiple auxiliary pole blocks 73 form a square structure around the upper main pole block 72, the poles of the auxiliary pole blocks 73 are arranged in the transverse direction, and the polarity of the side contacting the upper main pole block 72 is the same as that of the polarity of the pole adjacent to the top of the upper main pole block 72, thus, the upper main pole block 72 and the auxiliary pole block 73 may be in seamless assembly and close contact so as to produce no gap reluctance, so that the surface magnetic field intensity of the upper main pole block 72 is greatly increased to 10000 Gauss or above and the depth of action of the magnetic field is up to 1 m or so; of course, if a pole block is additionally arranged above the upper main pole block 72 and has the same structure as the upper main pole block 72, at this time, the pole block above the upper main pole block 72 may be regarded as a new upper main pole block 72, then the lateral side of the pole block above the upper main pole block 72 should also be provided with an auxiliary pole block 73, and the auxiliary pole block 73 on the lateral side of the upper main pole block 72 may be retained or removed; and in this solution, two magnetic assemblies 2 may be preferably arranged, and the polarities of the poles of the upper main pole blocks 72 of the two magnetic assemblies 2 adjacent to the top are opposite, thereby forming an excellent space magnetic field. The auxiliary pole block 73 and the upper main pole block 72 may be provided with transverse screw holes 888 that run through transversely, and are connected in series through a transverse bolt 889 and fixed through the nut 779 without gluing connection, so that the fixing effect is good, thereby effectively avoiding the drop of the magnetic field intensity due to the gap reluctance generated between the upper main pole block 72 and the auxiliary pole block 73.

Figure 5:
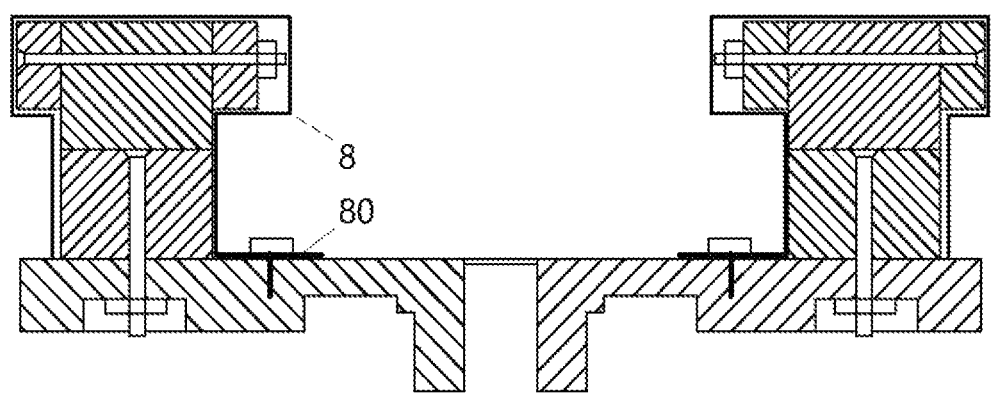
FIG. 5 is a cross-sectional structural view after the base revolving plate is assembled with the magnetic assembly according to embodiment 3 of the present disclosure.

Embodiment 3. As shown in FIG. 5, the difference from embodiment 1 or 2 lies in that a protective cover 8 is sleeved over the outer side of the magnetic assembly 2, a lower portion of the protective cover 8 extends to form a cover installation piece 80 for fixed connection with the base revolving plate 1, the cover installation piece 80 may be installed at and fixedly connected with the base revolving plate 1 through screws and the like, and the protective cover 8 is a non-magnetic isolation stainless steel cover, i.e., may be a non-magnetic isolation stainless steel housing, so as to provide a beautiful appearance, prevent the pole block from being oxidized, prevent the ferromagnetic object from direct collision and contact with the pole block, and also prevent the magnetic assembly 2 from falling off in the high-speed operation process, thereby further optimizing the structure and stress distribution, enhancing various physical properties and having a better magnetic therapy effect.

Figure 6:
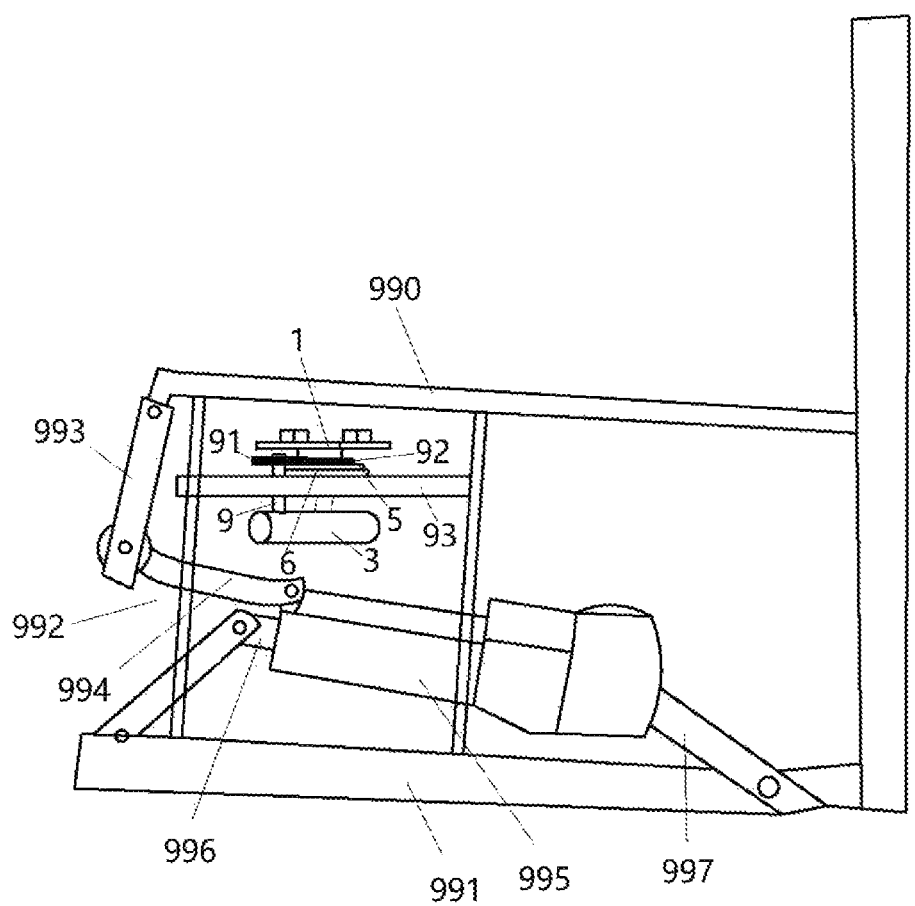
FIG. 6 is a perspective structural view of embodiment 4 of the present disclosure.

Embodiment 4. As shown in FIG. 6, a massage chair structure with a rotating magnet is provided. The device with a high energy rotating magnet according to any one of embodiments 1-3 is arranged below a seat 990 of the massage chair structure with a rotating magnet, a liftable telescopic footrest mechanism 992 for foot resting is arranged between the seat 990 and a chair bottom 991 of the massage chair structure with a rotating magnet, the telescopic footrest mechanism 992 comprises a reclining rod 993 hinged to the seat 990 and adjacent to the front side of the device with a high energy rotating magnet, a curved rod 994 hinged to the other end of the reclining rod 993 and located below the front portion of the device with a high energy rotating magnet and a retractable cylinder 995 hinged to the other end of the curved rod 994 and located below the device with a high energy rotating magnet, a piston rod 996 of the retractable cylinder 995 is hinged to a lower support rod 997, the other end of the lower support rod 997 is hinged to a position of the chair bottom 991 adjacent to the front end, a rear end of the retractable cylinder 995 is hinged to a position of the chair bottom 991 adjacent to the rear end, and the curved rod 994 may be provided with a curved portion that is arched in a direction away from the device with a high energy rotating magnet. The low-level triangular structure not only facilitates the placement of the device with a high energy rotating magnet having a larger volume, but also forms a sufficient space for a magnetic field to act, which is also advantageous for heat dissipation, muting, etc., and prevents the deformation operation of the chair lifting mechanism (such as the device with a high energy rotating magnet and the telescopic footrest mechanism 992) or a backrest pusher mechanism from producing interference or rubbing.

Figure 7:
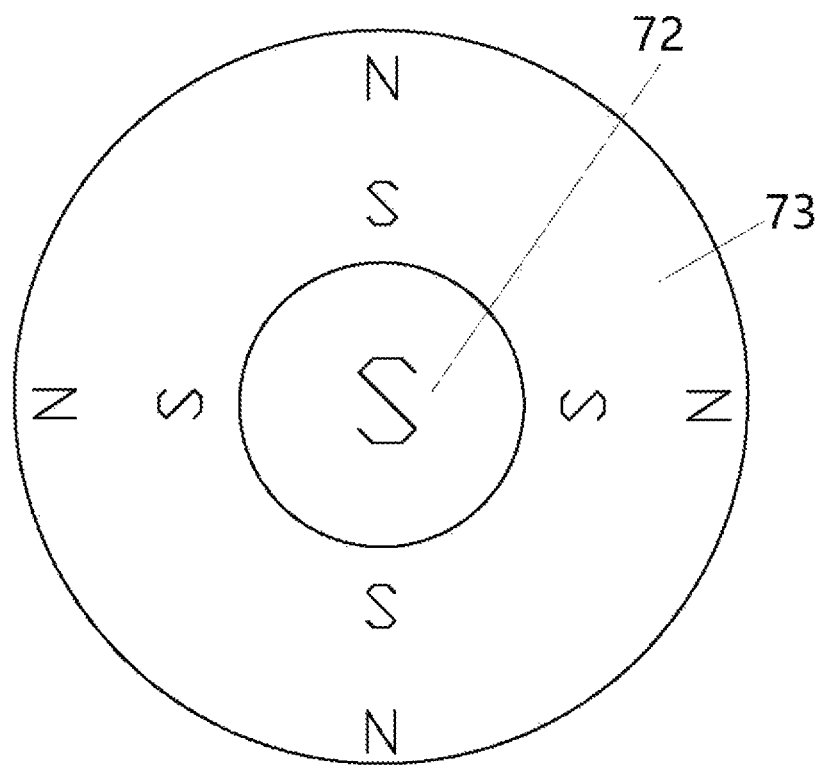
FIG. 7 is a top structural view of the design of one of the magnetic assemblies according to embodiment 4 of the present disclosure.
Figure 8:
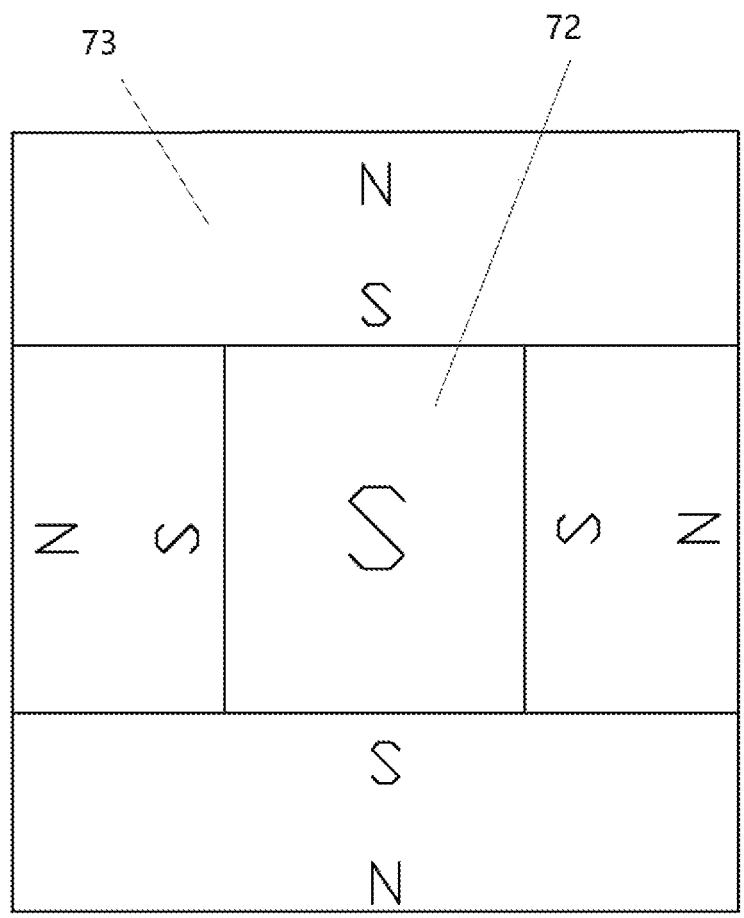
FIG. 8 is also a top structural view of the design of one of the magnetic assemblies according to embodiment 4 of the present disclosure.

Embodiment 5. As shown in FIG. 7 and FIG. 8, the difference from embodiment 2 lies in the design of the magnetic assembly 2. In the present embodiment, the upper main pole block 72 and the base main pole block 71 are arranged into a cylindrical structure, the auxiliary pole block 73 is arranged in a position of the upper main pole block 72 adjacent to the top, and may contact the lateral side of the upper main pole block 72 and have a sufficient distance from the base revolving plate 1 without contact; multiple auxiliary pole blocks 73 may be arranged and spliced into a square structure or annular structure to surround the upper main pole block 72, or a single square or annular auxiliary pole block 73 may be adopted to surround the upper main pole block 72; the poles of the base main pole block 71 and the upper main pole block 72 are respectively arranged along the vertical direction with the adjacent sides having the same polarity; the poles of the auxiliary pole blocks 73 are arranged in the transverse direction, and the polarity of the side contacting the upper main pole block 72 is the same as that of the polarity of the pole adjacent to the top of the upper main pole block 72; in addition, the base main pole block 71 and the upper main pole block 72 may be made into the same pole block; of course, the upper portion of the base revolving plate 1 may be only provided with the upper main pole block 72 and not provided with the base main pole block 71; and at this time, the upper main pole block 72 may be regarded as a single main pole block integrally formed from the base main pole block 71 and the upper main pole block 72, the auxiliary pole block 73 is arranged around the position of the single main pole block adjacent to the top, and the upper main pole block 72 may be directly sucked to the base revolving plate 1.

Embodiment 6. The difference from embodiment 1 or 2 lies in that the periphery of the device with a high energy rotating magnet is provided with an upper cover and a lower cover, the upper cover and the lower cover may be spliced and wrap the device with a high energy rotating magnet therein, the upper cover and the lower cover may be respectively a cover made of a polymer material such as plastics, and the upper cover and the lower cover may be respectively an arched bread-shaped cover that is symmetric up and down, and after being spliced, can effectively protect the device with a high energy rotating magnet and ensure the smooth operation of the device with a high energy rotating magnet.

Embodiment 7. The difference from embodiment 1 or 2 lies in the improvement on some components in embodiment 1 or 2. The center post 56 may be assembled from a bushing and a shaft; the center post 56 passes through a central region of the driving gear 92, namely a region of a center hole of the driving gear 92; the gears of the gear set 91 and the driving gear 92 may be plastic cement gears or plastic gears; the portion of the driving gear 92 adjacent to the central region extends upward to form an upper annular to-be-placed portion for the placement of the rotary auxiliary bearing 55, and the portion of the driving gear 92 adjacent to the central region extends downward to form a lower annular to-be-placed portion for the placement of the bearing inner ring 51; in addition, the bearing seat 6 may be used by the carrier bearing 5 corresponding to the driving gear 92, and at this time, may be designed in a circular shape; in fact, the bearing seat may also be used by the gear set 91, at this time, the bearing seat 6 may be designed in a drop shape or herringbone shape, and a corresponding bearing for the gear set 91 to use is arranged on the top; further, the gears of the gear set 91 may also be plastic cement gears or plastic gears; and the middle of the upper portion of the gear directly acting on the bearing extends upward to form a corresponding placement portion for the placement of the corresponding bearing, or the middle of the lower portion extends downward to form a placement portion for the placement of the corresponding bearing.

The specific embodiments are only an explanation of the present disclosure, and are not intended to limit the present disclosure. Those skilled in the art can make modifications without any creative contribution to the present embodiments as needed after reading this specification, however, these modifications are protected by the patent law as long as they are within the scope of the claims of the present disclosure.

What is claimed is:

1. A device with a rotating magnet, comprising: a vertically driven revolving axle positioned along a vertical axis and rotated in a horizontal plane, wherein the vertically driven revolving axle is connected to a motor; an upper end of the vertically driven revolving axle is connected to a gear set; the gear set meshes with a driving gear; a base revolving plate is fixed on an upper portion of the driving gear; and a magnetic assembly is installed on the base revolving plate;

wherein the magnetic assembly comprises a base main pole block installed on the base revolving plate;

wherein the magnetic assembly further comprises an upper main pole block; and the upper main pole block is arranged on an upper portion of the base main pole block;

wherein the magnetic assembly further comprises an auxiliary pole block, and the auxiliary pole block is arranged on a lateral side of the upper main pole block; and wherein the base main pole block is provided with a vertical screw hole running through from top to bottom of the base main pole block, the base revolving plate is provided with a corresponding installation screw hole, and a vertical bolt is arranged in the vertical screw hole, and the vertical bolt passes through the installation screw hole in the base revolving plate and is locked by a nut.

2. The device with a rotating magnet according to claim 1, wherein an assembly carrier is arranged below the driving gear.

3. The device with a rotating magnet according to claim 2, wherein the assembly carrier comprises a carrier bearing.

4. The device with a rotating magnet according to claim 3, wherein a bearing outer ring of the carrier bearing is installed on a supporting frame; the driving gear is arranged above a bearing inner ring of the carrier bearing; a rotary auxiliary bearing is arranged in a central region of the driving gear; and the supporting frame is provided with a center post over which an inner ring of the rotary auxiliary bearing is sleeved.

5. The device with a rotating magnet according to claim 1, wherein a protective cover is sleeved over an outer side of the magnetic assembly.

6. The device with a rotating magnet according to claim 5, wherein a lower portion of the protective cover extends to form a cover installation piece for fixed connection with the base revolving plate.

7. The device with a rotating magnet according to claim 1, wherein the base revolving plate is a magnetoconductive plate.

8. The device with a rotating magnet according to claim 1, wherein the driving gear is provided with a plurality of fixed installation holes in a circumferential array along the driving gear surface, and the driving gear is fixedly connected with the base revolving plate through retaining members; the base revolving plate is provided with corresponding installation holes.

9. The device with a rotating magnet according to claim 8, wherein the driving gear is integrally formed with gear stiffeners in the circumferential array with the gear stiffeners arranged between adjacent fixed installation holes.

10. The device with a rotating magnet according to claim 1, wherein a lower position of the base revolving plate is provided with a nut placement slot correspondingly communicating with the installation screw hole, and being configured for the nut to be placed.

11. The device with a rotating magnet according to claim 10, wherein the auxiliary pole block and the upper main pole block are provided with transverse screw holes that run through transversely, and are connected in series through a transverse bolt and fixed through the nut.

12. A massage chair structure with a rotating magnet, comprising:

a device with a rotating magnet comprising: a vertically driven revolving axle positioned along a vertical axis and rotated in a horizontal plane, wherein the vertically driven revolving axle is connected to a motor; an upper end of the vertically driven revolving axle is connected to a gear set; the gear set meshes with a driving gear; a base revolving plate is fixed on an upper portion of the driving gear; and a magnetic assembly is installed on the base revolving plate;

wherein the magnetic assembly comprises a base main pole block installed on the base revolving plate;

wherein the magnetic assembly further comprises an upper main pole block; and the upper main pole block is arranged on an upper portion of the base main pole block;

wherein the magnetic assembly further comprises an auxiliary pole block, and the auxiliary pole block is arranged on a lateral side of the upper main pole block; and wherein the base main pole block is provided with a vertical screw hole running through from top to bottom of the base main pole block, the base revolving plate is provided with a corresponding installation screw hole, and a vertical bolt is arranged in the vertical screw hole, and the vertical bolt passes through the installation screw hole in the base revolving plate and is locked by a nut;

wherein the device with the rotating magnet is arranged below a seat of the massage chair structure with the rotating magnet; a liftable telescopic footrest mechanism for foot resting is arranged between the seat and a chair bottom of the massage chair structure with the rotating magnet; the telescopic footrest mechanism comprises a reclining rod hinged to the seat and adjacent to the front side of the device with the rotating magnet; a curved rod hinged to the other end of the reclining rod and located below the front portion of the device with the rotating magnet and a retractable cylinder hinged to the other end of the curved rod and located below the device with the rotating magnet; a piston rod of the retractable cylinder is hinged to a lower support rod; an other end of the lower support rod is hinged to a position located in a front end of the chair bottom; and a rear end of the retractable cylinder is hinged to a position located in a rear end of the chair bottom.

* * * * *